US012636331B2

(12) United States Patent
Yoon et al.

(10) Patent No.: US 12,636,331 B2
(45) Date of Patent: May 26, 2026

(54) COMPOSITION FOR PREVENTING OR TREATING LUNG CANCER, COMPRISING A COMPOUND ISOLATED FROM CEPHALOTAXUS EXTRACT AS AN ACTIVE INGREDIENT

(71) Applicants: NATIONAL CANCER CENTER, Goyang-si (KR); NATIONAL INSTITUTE FOR KOREAN MEDICINE DEVELOPMENT, Gyeongsan-si (KR)

(72) Inventors: Kyung Sil Yoon, Goyang-si (KR); Yong Nyun Kim, Seoul (KR); Jae Gal Shim, Seoul (KR); Dong Hoon Shin, Seoul (KR); Hyo Jung Kim, Daegu (KR); Myoung Lae Cho, Gyeongsan-si (KR); Soo Hyun Kim, Daegu (KR)

(73) Assignees: NATIONAL CANCER CENTER, Goyang-si (KR); NATIONAL INSTITUTE FOR KOREAN MEDICINE DEVELOPMENT, Gyeongsan-si (KR)

( * ) Notice: Subject to any disclaimer, the term of this patent is extended or adjusted under 35 U.S.C. 154(b) by 386 days.

(21) Appl. No.: 18/249,202

(22) PCT Filed: Oct. 5, 2021

(86) PCT No.: PCT/KR2021/013591
§ 371 (c)(1),
(2) Date: Apr. 14, 2023

(87) PCT Pub. No.: WO2022/080729
PCT Pub. Date: Apr. 21, 2022

(65) Prior Publication Data

US 2024/0058405 A1 Feb. 22, 2024

(30) Foreign Application Priority Data

Oct. 16, 2020 (KR) ........................ 10-2020-0134470

(51) Int. Cl.
*A61K 36/13* (2006.01)
*A61K 31/55* (2006.01)
*A61K 31/7088* (2006.01)
*A61K 33/243* (2019.01)
*A61P 35/00* (2006.01)

(52) U.S. Cl.
CPC .............. *A61K 36/13* (2013.01); *A61K 31/55* (2013.01); *A61K 31/7088* (2013.01); *A61K 33/243* (2019.01); *A61P 35/00* (2018.01)

(58) Field of Classification Search
CPC .. A61K 36/185; A61K 31/713; A61K 33/243; A61K 2300/00; A61K 31/7088; A61P 35/00; A23L 33/105
See application file for complete search history.

(56) References Cited

U.S. PATENT DOCUMENTS

2005/0090484 A1* 4/2005 Robin ..................... A61P 43/00 514/214.03
2007/0166415 A1* 7/2007 Liu ...................... A61K 36/185 424/769
2009/0306130 A1* 12/2009 Weber ..................... A61P 35/00 514/307
2018/0147142 A1* 5/2018 Knight .................... A61P 25/28
2019/0161493 A1* 5/2019 Robin ................ C07D 491/147

FOREIGN PATENT DOCUMENTS

KR 1999-000203 A 1/1999
KR 10-1825637 B1 2/2018
KR 10-2018-0085124 A 7/2018
KR 10-2020-0059921 A 5/2020

OTHER PUBLICATIONS

Yuan et al. Biotechnology Letters, 20, 1, 1998, 63-66.*
American Cancer Society: Lung Cancer, 2 pgs, 2024.*
International Search Report issued Jan. 24, 2022 in PCT/KR2021/013591, filed on Oct. 5, 2021, 2 pages.
Joelle Perard-Viret et al. "Chapter Four-Cephalotaxus Alkaloids", The Alkaloids: Chemistry and Biology, vol. 78, 2017, pp. 205-352.
Manasses K. Yunmham et al., "Combinatorial treatment of ovarian cancer cells with harringtonine and cisplatin results in increased cisplatin-DNA adducts", Oncology Reports 11: 833-838, 2004.
Kee Dong Yoon et al., "A New Neolignan from *Cephalotaxus koreana*", Bull. Korean Chem. Soc. 2010, vol. 31, No. 2, pp. 495-496.
Bing Zhu et al., "Overexpression of NR4A1 is associated with tumor recurrence and poor survival in non-small-cell lung carcinoma", Oncotarget, 2017, vol. 8, (No. 69), pp. 113977-113986.

(Continued)

*Primary Examiner* — Kyle A Purdy

(74) *Attorney, Agent, or Firm* — Oblon, McClelland, Maier & Neustadt, L.L.P.

(57) ABSTRACT

The present disclosure relates to a composition for preventing or treating lung cancer, comprising a compound isolated from a *Cephalotaxus* extract as an active ingredient. Isoharringtonine, which is the compound isolated from the *Cephalotaxus* extract according to the present disclosure, induces apoptosis and exhibits the effect of inhibiting the growth of non-small cell lung cancer cell lines, and thus can be useful in the prevention or treatment of lung cancer.

In addition, the combined treatment of isoharringtonine and siNR4A1 enhances anticancer activity, and the combined treatment of isoharringtonine and cisplatin, which is a conventional anticancer drug, induces a high anticancer effect at a low concentration of cisplatin, thereby reducing side effects of anticancer treatment.

15 Claims, 8 Drawing Sheets

Specification includes a Sequence Listing.

(56) References Cited

OTHER PUBLICATIONS

Dezhi Liu et al., "Genistein enhances the effect of cisplatin on the inhibition of non-small cell lung cancer A549 cell growth in vitro and in vivo", Oncology Letters 8: 2806-2810, 2014.

"Development of anti-cancer peptide targeting non-small cell lung cancer from insect protein", (Development of targeted anticancer peptides for non-small cell lung cancer from insect proteins), Final report on completed tasks, (Assignment No. PJ012284), 2019, (with English Summary and Unedited Computer-Generated English Translation), 81 pages.

Bing Zhu et al., "Overexpression of NR4A1 is associated with tumor recurrence and poor survival in non-small-cell lung carcinoma", Oncotarget, 2017, vol. 8, (No. 69), p. 113977-113986.

* cited by examiner

Isoharringtonine

SEQUENCE LISTING

```
<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: siNR4A1_1

<400> SEQUENCE: 1

gagcuauucc augccuacg                                          19


<210> SEQ ID NO 2
<211> LENGTH: 19
<212> TYPE: RNA
<213> ORGANISM: Artificial Sequence
<220> FEATURE:
<223> OTHER INFORMATION: siNR4A1_2
```

-continued

<400> SEQUENCE: 2
ggauacugga uacacccgu 19

COMPOSITION FOR PREVENTING OR TREATING LUNG CANCER, COMPRISING A COMPOUND ISOLATED FROM CEPHALOTAXUS EXTRACT AS AN ACTIVE INGREDIENT

CROSS-REFERENCE TO RELATED APPLICATIONS

The present application is a 35 U.S.C. § 371 National Stage Application of International Patent Application PCT/KR2021/013591, filed Oct. 5, 2021, which is based on and claims the benefit of priority to Korean Application No. 10-2020-0134470, filed Oct. 16, 2020. The entire contents of these applications are incorporated herein by reference.

TECHNICAL FIELD

The present disclosure relates to a composition for preventing or treating lung cancer, comprising a compound isolated from a *Cephalotaxus* extract as an active ingredient.

BACKGROUND ART

Lung cancer not only has a high incidence rate but also shows a very high mortality rate. Lung cancer is largely composed of small cell lung cancer and non-small cell lung cancer, and 80% or higher of lung cancers belongs to non-small cell lung cancers. Non-small cell lung cancer is divided into squamous cell carcinoma, adenocarcinoma and giant cell tumor. Due to the difficulty of early diagnosis, anticancer chemotherapy has been mainly used for the late stage-lung cancers or used as an adjuvant therapy assisting surgery or radiation therapy, but there is a need to improve the therapeutic effect because of the low survival rate of lung cancer patients.

Recently, molecular target therapy and immunotherapy led remarkable advance in treating non-small cell lung cancer. However, the majority of patients are not candidates for such treatment, and traditional anticancer therapy based on cisplatin is still being performed for lung cancer patients who have acquired resistance to existing therapies. Therefore, there is a need for new anticancer agents or combination therapies that can increase the efficiency of anticancer therapies in the patient population.

Solid tumors in a human body grows in three dimensions (3D), so that they are differently exposed not only to physicochemical stress, but also to oxygen and nutrients, metabolites, signal transmitters, and the like. Solid tumors grow fast but angiogenesis are not sufficient enough to support tumor growth, so that most of them are in a state of lack of oxygen and nutrients inside. In order for cancer cells to survive in such an environment, changes are generated for achieving metabolic adaptation, activating survival pathways, promoting angiogenesis, and the like. Therefore, it cannot be reproduced in two-dimensional culture with sufficient supply of oxygen and nutrients, which is mainly used for various cancer studies at the cellular level. Thus, in order to understand the pathology of cancer occurring in the human body or to evaluate the efficacy of anticancer drugs, it is essential to maintain a state similar to the 3D structure of tissues even in cell culture.

Because the sensitivity of anticancer therapy is modulated by variables such as cell-to-cell contact, cell communication, oxygen and substance concentrations, and cell state, the 3D tumorspheroid system is a model useful for anticancer drug research, and cellular responses of tumorspheroid after treating with anticancer drugs are more similar to cellular responses in tumors in vivo.

*Cephalotaxus* is a tree belonging to the family Cephalotaxaceae, examples of which include *Cephalotaxus koreana* Nakai, *Cephalotaxus harringtonia* var. *nana* (Nakai) Rehder, *Cephalotaxus harringtonia* K. Koch, *Cephalotaxus harringtonia* var. fastigiate, and the like. Cephalotaxaceae *koreana* Nakai is a species native to the Korean Peninsula, is mainly distributed in the south of the central region, and is also known to grow in Eastern Asia such as China and Japan as well as in the Himalayas. Generally, this is an evergreen coniferous tree that reaches about 3 meters in height, whose bark is dark brown, and split vertically. In oriental medicine, the red fruit of Cephalotaxaceae *koreana* Nakai is called *Cephalotaxus harringtonia* (Knight) K. Koch, and has been used as antiparasitic, constipation, cough, sputum, and tonic.

The present inventors have confirmed that the compound isolated from a *Cephalotaxus* extract has a preventive or therapeutic effect on lung cancer, thereby completing the present disclosure.

DETAILED DESCRIPTION OF THE INVENTION

Technical Problem

It is an object of the present disclosure to provide a pharmaceutical composition or a health functional food composition for preventing or treating lung cancer, comprising a compound isolated from a *Cephalotaxus* extract as an active ingredient.

Technical Solution

In order to achieve the above object, according to one aspect of the present disclosure, there is provided a pharmaceutical composition for preventing or treating lung cancer, comprising a compound isolated from a *Cephalotaxus* extract as an active ingredient.

The *Cephalotaxus* may be one or more selected from the group consisting of *Cephalotaxus koreana, Cephalotaxus fortunei, Cephalotaxus griffithii, Cephalotaxus hainanensis, Cephalotaxus lanceolata, Cephalotaxus latifolia, Cephalotaxus mannii, Cephalotaxus oliveri, Cephalotaxus sinensis* and *Cephalotaxus wilsoniana.*

The extract may be obtained by extracting the *Cephalotaxus* with water, C1~C4 alcohol, or a mixed solvent thereof.

The isolated compound may be one or more selected from the group consisting of isoharringtonine, harringtonine, homoharringtonine, nordeoxyharringtonine and homodeoxyharringtonine.

The lung cancer may be non-small cell lung cancer or lung cancer showing resistance to EGFR-TKIs.

The composition may inhibit tumorspheroid growth through apoptosis.

The composition may further comprise siNR4A1.

The composition may further comprise cisplatin.

According to another aspect of the present disclosure, there is provided a health functional food composition for preventing or treating lung cancer, comprising a compound isolated from a *Cephalotaxus* extract as an active ingredient.

The isolated compound may be one or more selected from the group consisting of isoharringtonine, harringtonine, homoharringtonine, nordeoxyharringtonine and homodeoxyharringtonine.

According to yet another aspect of the present disclosure, there is provided a method for preventing or treating lung cancer comprising the step of administering a compound isolated from a *Cephalotaxus* extract to a non-human subject.

Advantageous Effects

Isoharringtonine, which is the compound isolated from the *Cephalotaxus* extract according to the present disclosure, induces apoptosis and exhibits the effect of inhibiting the growth of non-small cell lung cancer cell lines, and thus can be useful in the prevention or treatment of lung cancer.

In addition, by performing the combined treatment of isoharringtonine and siNR4A1, anticancer activity can be increased, and when performing the combined treatment of isoharringtonine and cisplatin, which is a conventional anticancer drug, a high anticancer effect can be induced by treating a low concentration of cisplatin, thereby reducing side effects of anticancer treatment.

DETAILED DESCRIPTION OF THE EMBODIMENTS

Figure 1:
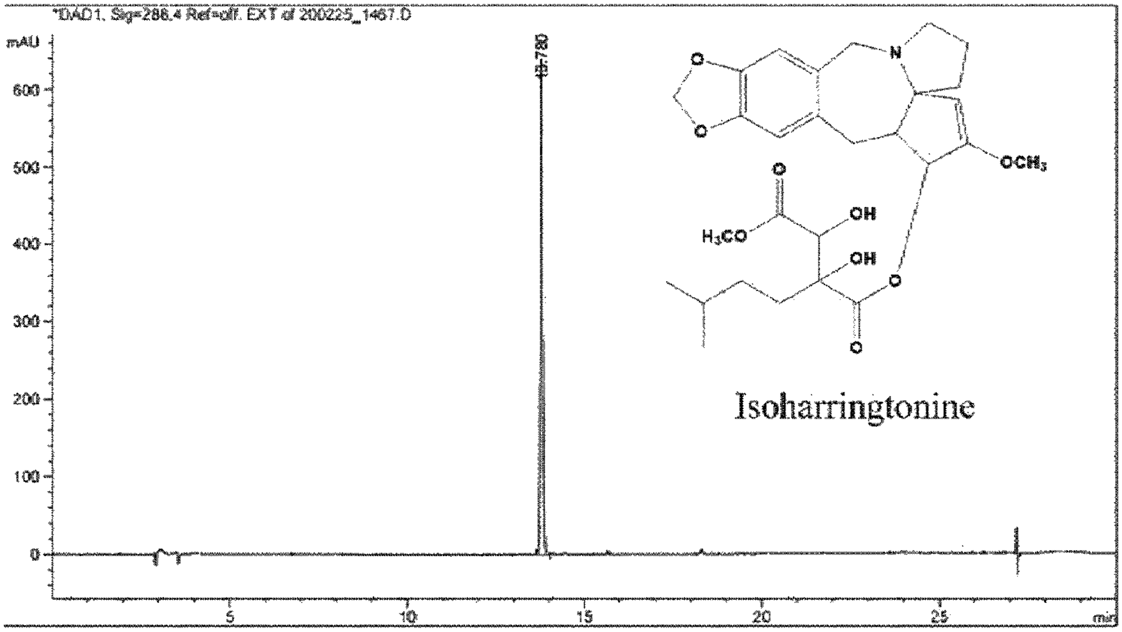
FIG. 1 shows the chromatogram and chemical structure of isoharringtonine (IHT) isolated from a *Cephalotaxus* extract.

The present inventors have confirmed that the compound isolated from a *Cephalotaxus* extract has a preventive or therapeutic effect on lung cancer, thereby completing the present disclosure.

Specifically, the present disclosure relates to a pharmaceutical composition for preventing or treating lung cancer, comprising a compound isolated from a *Cephalotaxus* extract as an active ingredient.

The "*Cephalotaxus*" as used herein may be one or more selected from the group consisting of *Cephalotaxus koreana, Cephalotaxus fortunei, Cephalotaxus griffithii, Cephalotaxus hainanensis, Cephalotaxus lanceolata, Cephalotaxus latifolia, Cephalotaxus mannii, Cephalotaxus oliveri, Cephalotaxus sinensis* and *Cephalotaxus wilsoniana*. In Production Example of the present disclosure, *Cephalotaxus koreana* was used.

The *Cephalotaxus* may be wild or commercially available, and roots, stems, leaves or flowers of this plant can be used, but are not limited thereto.

The extract may be obtained using conventional extraction methods known in the art, such as filtration, hot water extraction, immersion extraction, reflux cooling extraction, and ultrasonic extraction, but is not limited thereto. The extract can be obtained by extracting the *Cephalotaxus* with water, a C1~C4 alcohol, or a mixed solvent thereof, but is not limited thereto. When a lower alcohol is used as the extraction solvent, it is more preferably selected from methanol or ethanol. The extract of the present disclosure includes not only the extract by the above-mentioned extraction solvent, but also an extract obtained through other conventional extraction methods or an extract that has passed through a purification and fermentation process. Active fractions obtained through various purification and extraction methods, such as extraction by supercritical carbon dioxide in high temperature and reduced pressure, extraction using ultrasonic waves, extracts obtained from fermentation products using an ultrafiltration membrane with a certain molecular weight cut-off value, isolated by various chromatography methods, or natural conditions or various microorganisms, are also included in the extract of the present disclosure.

The isolated compound is one or more selected from the group consisting of isoharringtonine, harringtonine, homoharringtonine, nordeoxyharringtonine and homodeoxyharringtonine, but is not limited thereto.

"Isoharringtonine" as used herein has a structure represented by the following Chemical Formula 1. In Production Example of the present disclosure, isoharringtonine was isolated from the leaf extract of *Cephalotaxus*, and the anticancer activity was evaluated using the isolated isoharringtonine.

[Chemical Formula 1]

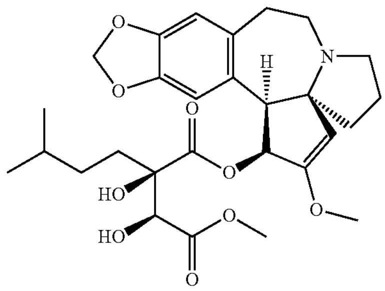

"Harringtonine" as used herein is 2-hydroxy-2-(3-hydroxy-3-methylbutyl)butanedioic acid 1-[(3S)-3-deoxy-cephalotaxine-3-yl]4-methyl ester, and has a molecular formula of C28H37NO$_9$, and a structure of the following Chemical Formula 2.

[Chemical Formula 2]

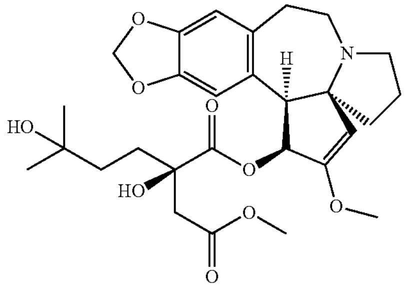

"Homoharringtonine" as used herein has a molecular formula of $C_{29}H_{39}NO_9$ and a structure represented by the following Chemical Formula 3.

[Chemical Formula 3]

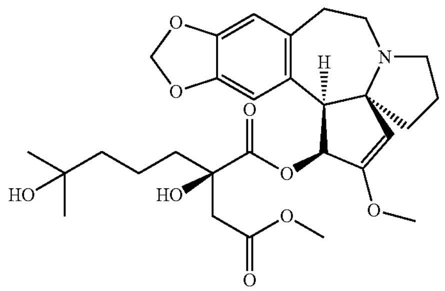

"Nordeoxyharringtonine" as used herein has a molecular formula of $C_{29}H_{39}NO_9$ and a structure represented by the following Chemical Formula 4.

[Chemical Formula 4]

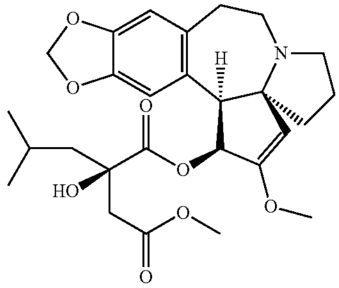

"Homodeoxyharringtonine" as used herein has a molecular formula of $C_{29}H_{39}NO_8$ and a structure represented by the following Chemical Formula 5.

[Chemical Formula 5]

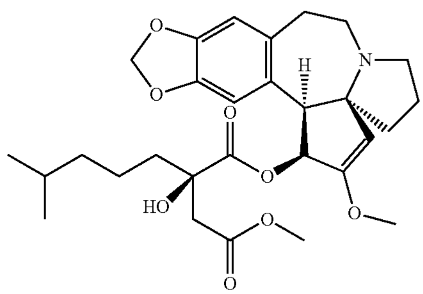

"Lung cancer" as used herein may be a non-small cell lung cancer (NSCLC) or a lung cancer showing resistance to EGFR-TKIs, but is not limited thereto.

The non-small cell lung cancer is a type of epithelial carcinoma, and refers to all epithelial lung cancers other than small cell lung cancer, and accounts for about 85% to 90% of all lung cancers. The non-small cell lung cancer is relatively less sensitive to chemotherapy as compared to the small cell lung cancer, and divides cancer stages based on the TNM classification system: the size of tumor, the extent of cancer spread to regional lymph nodes, and the presence or absence of cancer metastasis. In the treatment of non-small cell lung cancer, since early non-metastatic non-small cell lung cancer has very low sensitivity to chemotherapy and radiation, surgery is generally performed together with platinum-based ancillary chemotherapy. On the other hand, in the case of a metastatic non-small cell lung cancer that has passed the early stages, various chemotherapies are used. Symptoms of non-small cell lung cancer include persistent cough, chest pain, weight loss, nail damage, joint pain, shortness of breath, and the like, but because the non-small cell lung cancer usually progresses slowly, the symptoms are rarely seen in the early stages. In one embodiment of the present disclosure, the anticancer activity of isoharringtonine was tested using A549 and NCI-H460 cell lines which are non-small cell lung cancer cell lines.

In one embodiment of the present disclosure, as a result of measuring multivulva, which means the proliferation of *C. elegans* that express EGFR-L858R and T790M showing resistance to EGFR-TKIs, it was confirmed that treatment with high concentrations of isoharringtonine inhibits multivulva, and combined treatment with low concentrations of isoharringtonine and siNR4A1 has a significant inhibitory effect on multivulva (Example 4). Therefore, the composition of the present disclosure can be applied to lung cancer cells showing resistance to EGFR-TKIs.

Figure 4:
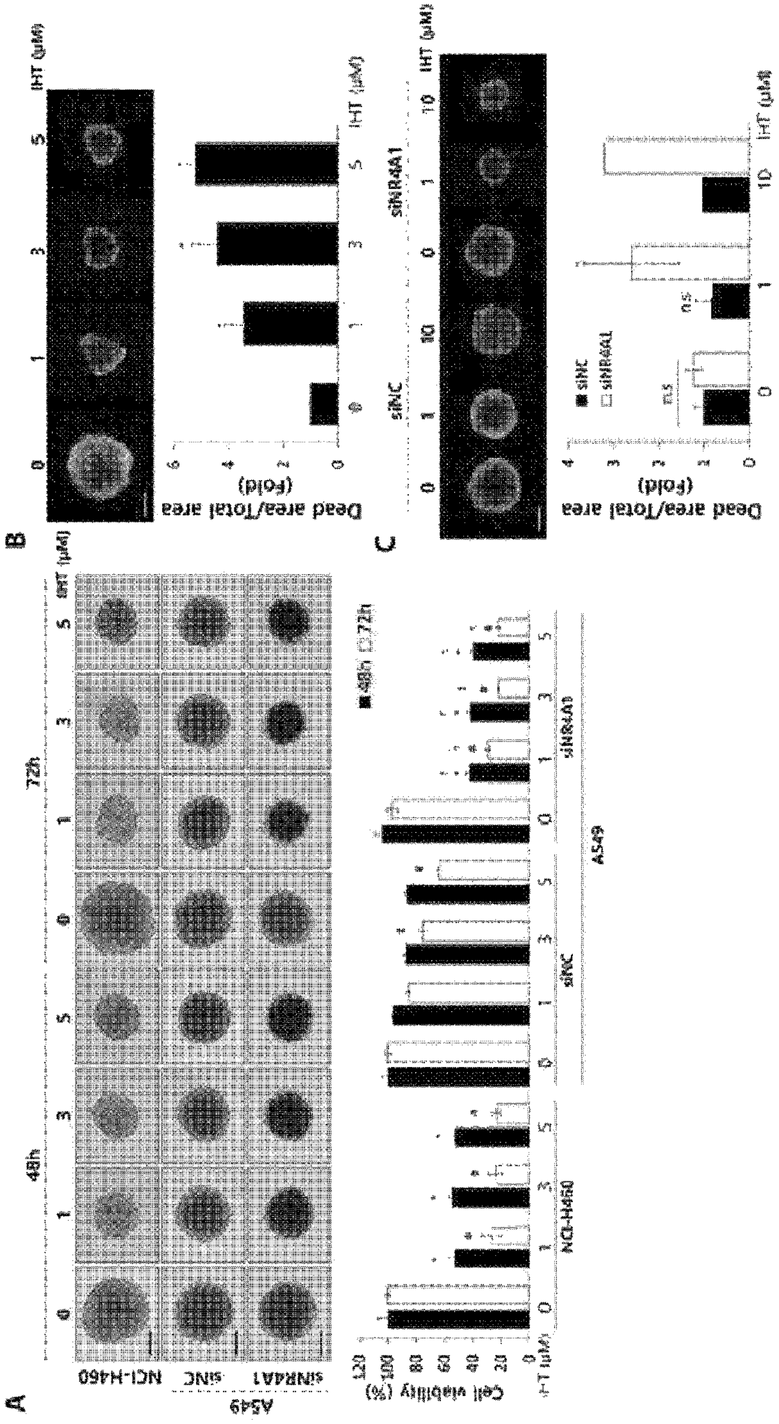
FIG. 4 shows the effect of isoharringtonine (IHT) on tumorspheroid growth inhibition and cell death induction.
Figure 5:
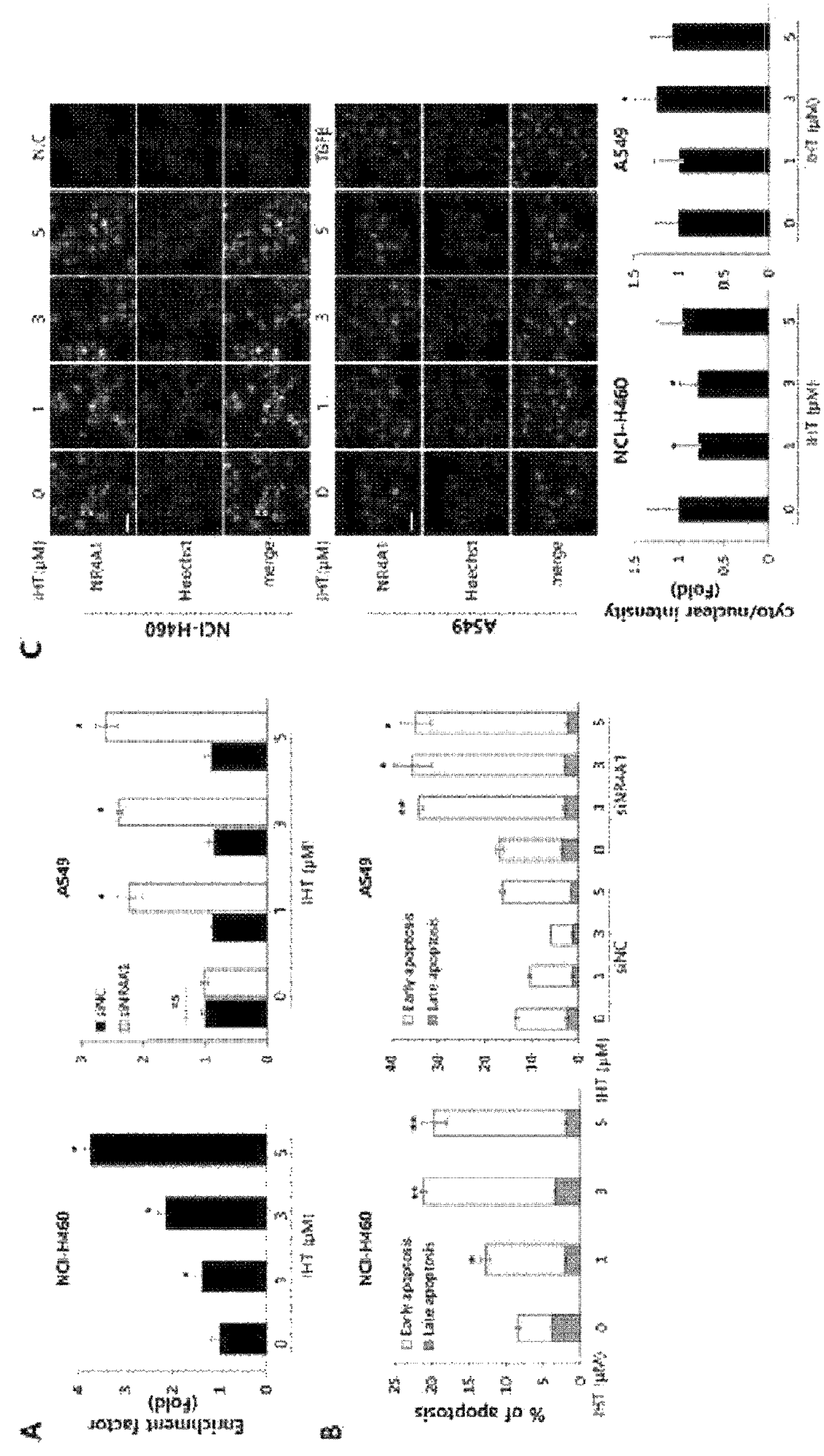
FIG. 5 confirms apoptosis induced in tumorspheroids.
Figure 6:
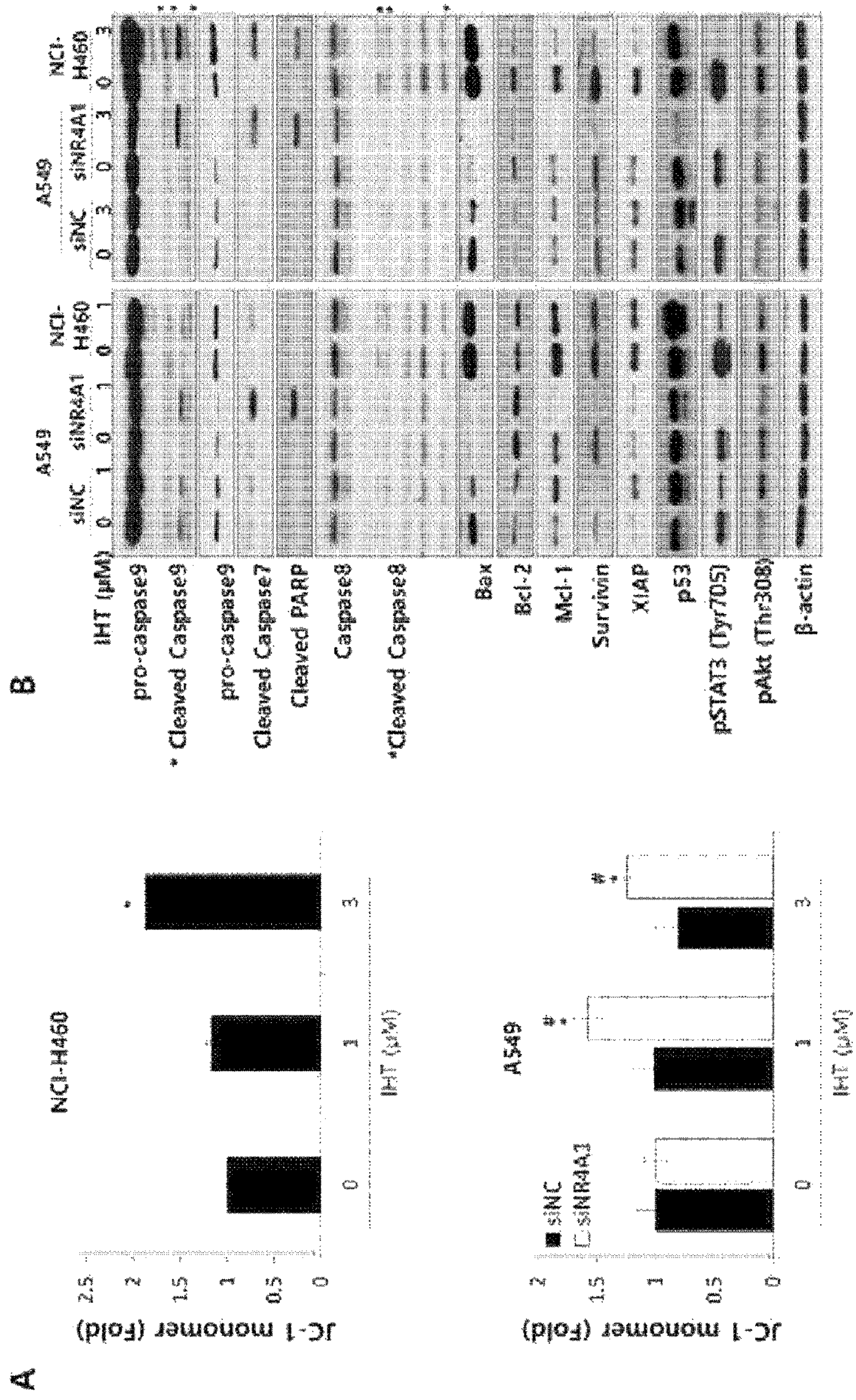
FIG. 6 analyzes the apoptosis-inducing mechanism of isoharringtonine (IHT).

In one embodiment of the present disclosure, the effects of isoharringtonine on growth inhibition and cell death induction of the tumorspheroids were observed (FIG. 4), and it was confirmed that cell death induced in tumorspheroids was apoptosis (FIG. 5). Further, it was confirmed that it induces apoptosis by activating the intrinsic pathway via mitochondria (FIG. 6).

Figure 7:
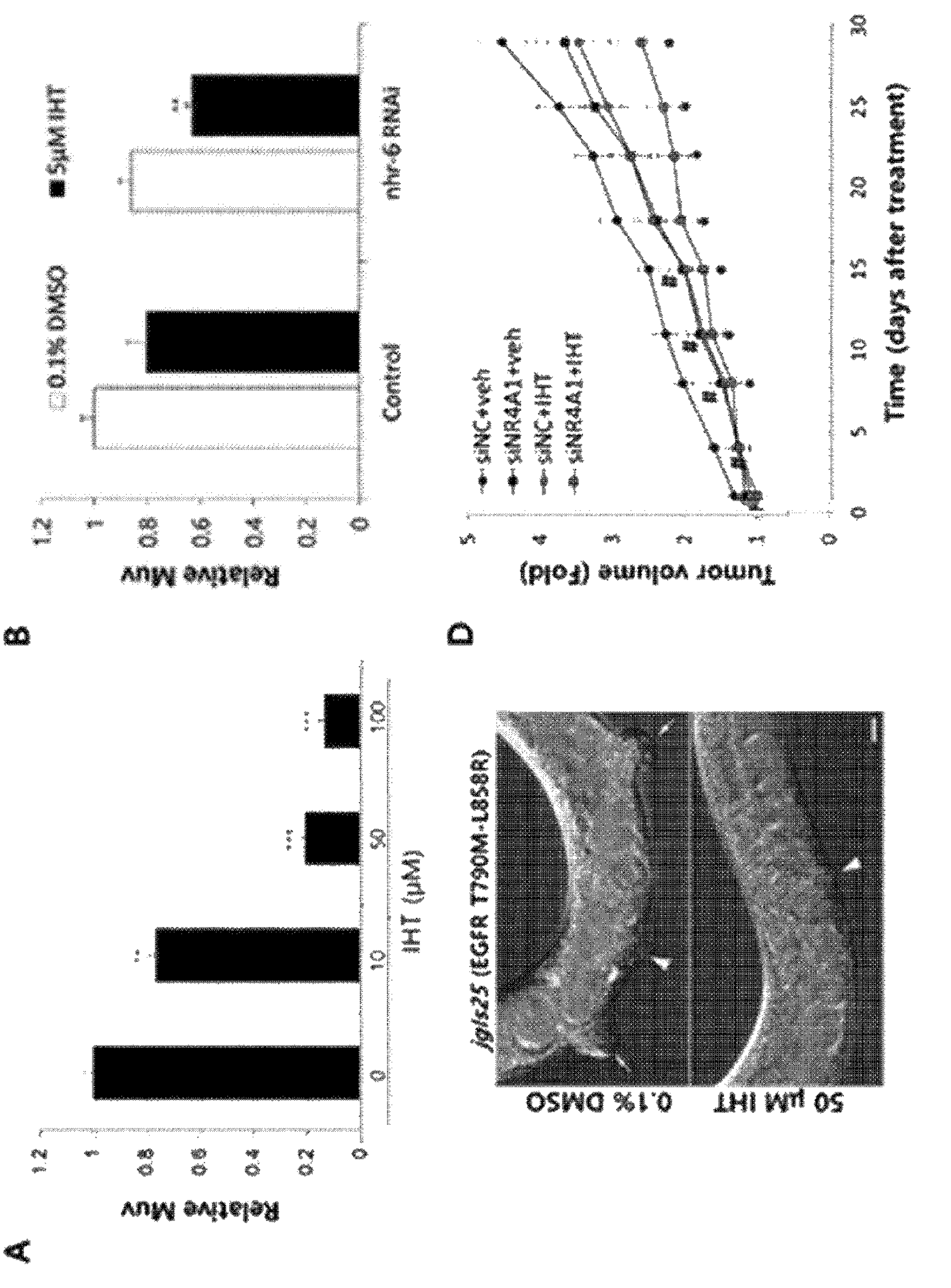
FIG. 7 shows combined therapeutic effects of isoharringtonine (IHT) and siNR4A1.
Figure 8:
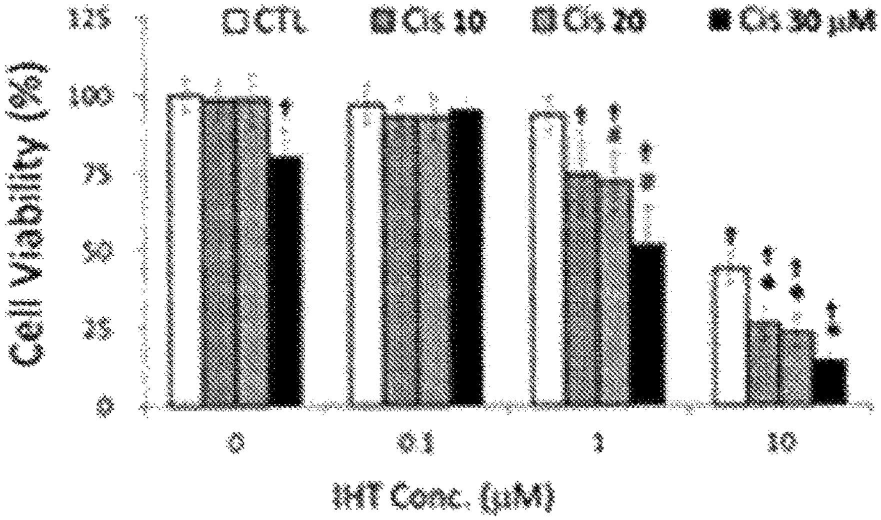
FIG. 8 shows combined therapeutic effects of isoharringtonine (IHT) and cisplatin.

In addition, in one embodiment of the present disclosure, it was confirmed that anticancer activity is exhibited not only when treating isoharringtonine at a high concentration, but also when treating it at a low concentration in combination with siNR4A1 (FIG. 7), and it was also confirmed that when performing the combined treatment of conventional anticancer drugs, cisplatin and isoharringtonine, a high anticancer effect is induced even at a low concentration of cisplatin (FIG. 8). The pharmaceutical composition of the present disclosure can be administered in a pharmaceutically effective amount. The term "pharmaceutically effective amount" as used herein refers to an amount which is sufficient to treat the disease at a reasonable benefit/risk ratio applicable for any medical treatment. The level of effective amount can be determined depending on the type, seventy, age, and sex of a subject, the type of a disease, the activity of a drug, the sensitivity to the drug, an administration time, a route of administration, and a secretion rate, a therapeutic period, factors including drugs to be used together, and other factors well known in the field of medicine. The composition of the present invention may be administered as subject therapy or may be administered in combination with other therapies, and it can be administered sequentially or concurrently with conventional therapeutic agents. And, the composition may be administered in a single dose or multiple doses. By considering all the above factors, it is important to administer the composition at a dose in which the maximum effect can be achieved without any side effects when administered at a minimum dose. Thus, the dose of the composition may be easily determined by those skilled in the related art.

The pharmaceutical composition of the present disclosure is applicable to any subjects without any particular limitation as long as the pharmaceutical composition targets the treatment or prevention of respiratory diseases. For example, any of non-human animals such as a monkey, a dog, a cat, a rabbit, a guinea pig, a rat, a mouse, cattle, a sheep, a pig, a goat, etc., human beings, birds, and fishes can be used. The pharmaceutical composition may be parenterally, subcutaneously, intraperitoneally, intrapulmonarily and intranasally administered, and may be administered using a proper method including intralesional administration for local treatment, when necessary. A preferred dose of the pharmaceutical composition according to the present disclosure may vary depending on the condition and weight of a subject, the severity of a disease, the shape of a drug, a route of administration, and an administration period, but may be properly chosen by those skilled in the related art. For example, the pharmaceutical composition may be orally, intrarectally or intravenously administered, or may be administered by intramuscular, subcutaneous, endocervical or intracerebrovascular injection, but the present disclosure is not limited thereto.

The pharmaceutical composition may be prepared into any one formulation selected from the group consisting of a tablet, a pill, a powder, a granule, a capsule, a suspension, a liquid for internal use, an emulsion, a syrup, a sterile aqueous solution, a non-aqueous solvent, a suspension, an emulsion, a freeze-drying agent, and a suppository, and also prepared into various formulations for oral or parenteral administration. When formulated, the composition may be prepared using a diluent or excipient generally used in the related art, such as a filler, a bulking agent, a binder, a wetting agent, a disintegrating agent, a surfactant, etc.

A solid preparation for oral administration includes a tablet, a pill, a powder, a granule, a capsule, etc. Such a solid preparation may be prepared by mixing at least one excipient, for example, starch, calcium carbonate, sucrose or lactose, gelatin and the like, with one or more compounds. Also, lubricants such as magnesium stearate, talc and the like may be used in addition to the simple excipients. A liquid preparation for oral administration includes a suspension, a liquid for internal use, an emulsion, a syrup, etc. In this case, the liquid preparation includes various excipients, for example, a wetting agent, a sweetening agent, a flavoring agent, a preservative, and the like in addition to the generally used simple diluents such as water, liquid paraffin, etc. A preparation for parenteral administration includes a sterile aqueous solution, a non-aqueous solvent, a suspension, an emulsion, a freeze-dried preparation, a suppository, etc. Propylene glycol, polyethylene glycol, and a vegetable oil such as olive oil, an injectable ester such as ethyl oleate, and the like may be used as the non-aqueous solvent and the suspending agent. Witepsol, Macrogol, Tween 61, cacao butter, laurin butter, glycerogelatin, and the like may be used as a base of the suppository.

The total daily dose of the composition suitable for use may be determined by prescription within the scope of medical judgment. In this case, the composition may be generally administered at a dose of 0.001 to 1,000 mg/kg, preferably 0.05 to 200 mg/kg, more preferably 0.1 to 100 mg/kg once or several times a day.

Further, the present disclosure relates to a health functional food composition for preventing or treating lung cancer, comprising a compound isolated from a *Cephalotaxus* extract as an active ingredient.

The "health functional food" as used herein refers to a food which is prepared and processed in the form of a tablet, a capsule, a powder, a granule, a liquid, and a pill using crude materials or components which have functionality beneficial to the human body. Here, the term "functionality" refers to a situation in which nutriments are regulated with respect to the structure and function of the human body, or an effect useful for health care such as a physiological effect is achieved. The health functional food according to the present invention may be prepared using methods generally used in the related art, and may be prepared by adding raw materials and components which are generally added in the related art in the preparation of the health functional food. Also, the health functional food has advantages in that the health functional food has no side effects which may occur upon long-term use of drugs since the food is used as a raw material unlike common drugs, and may be highly portable.

The food composition according to the present invention may be included in the form of a pill, a powder, a granule, an infusum, a tablet, a capsule, or a solution. Types of foods are not particularly limited, and include, for example, various drinks, gums, tea, vitamin complex, health food supplements, etc.

In addition to the compound isolated from the *Cephalotaxus* extract, other components may be added to the food composition, and types of the other components are not particularly limited. For example, like conventional foods, various herbal extracts, sitologically acceptable auxiliary food additives, or natural carbohydrates may be included as additional components, but the present invention is not limited thereto.

The "auxiliary food additive" as used herein refers to a component that may be auxiliarily added to foods, and thus may be added to prepare health functional foods for subject formulations, and may be properly selected and used by those skilled in the related art. Examples of the auxiliary food additive include various nutrients, vitamins, minerals (electrolytes), flavoring agents such as synthetic and natural flavoring agents, coloring agents and fillers, pectic acid and salts thereof, alginic acid and salts thereof, organic acids, protective colloid thickening agents, pH regulators, stabilizing agents, preservatives, glycerin, alcohols, carbonating agents used for carbonated drinks, etc., but types of the auxiliary food additives according to the present invention are not limited to the above listed examples of the auxiliary food additive.

Examples of the natural carbohydrates include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. In addition to the above-listed flavoring agents, natural flavoring agents (thaumatin, etc.), *Stevia* extracts (rebaudioside A, glycyrrhizin, etc.), and synthetic flavoring agents (saccharin, aspartame, etc.) may be used as the flavoring agent.

In addition, the present disclosure relates to a method for preventing or treating lung cancer comprising the step of administering a compound isolated from a *Cephalotaxus* extract to a non-human subject.

MODE FOR INVENTION

Hereinafter, the configurations and effects of the present disclosure will be described in further detail with reference to examples thereof. However, it should be understood that the following examples are for illustrative purposes only and is not intended to limit or define the scope of the invention.

[Production Example] Isolation of *Cephalotaxus* Extract and Isoharringtonine 1.5 kg of *Cephalotaxus koreana* leaves in the family Cephalotaxaceae were extracted twice for 180 minutes with an ultrasonic extractor by adding 15 L of methanol, and then the extract was filtered using No. 2 filter paper, and the obtained filtrate was concentrated under reduced pressure to obtain a methanol extract. The methanol extract (228 g) was suspended in water and then sequentially fractionated according to polarity using hexane, ethyl acetate and butanol to obtain a butanol soluble material. Then, butanol soluble material (67 g) was eluted with the solvent condition of Equation 1 using silica gel chromatography to obtain a total of 10 fractions.

$CH_2Cl_2$—MeOH=20:1→10:1 [Equation 1]

ACN-ammonium carbonate=30:70→50:50 [Equation 2]

Of the 10 fractions, the 4th fraction was subjected to silica gel CC and eluted again under the solvent conditions of Equation 1 to obtain a total of 20 fractions. Of the 20 fractions, the 9th fraction was continuously isolated using RP-HPLC (ODS H-80, 250×20 mm ID) using the solvent conditions of Equation 2, and then 71 mg of isoharringtonine of the following Chemical Formula 1 was secured. The IHT structure was confirmed by nuclear magnetic resonance analysis, and compared and determined with previously reported spectroscopic data (Weisleder, D., R. G. Powell, and C. R. Smith Jr., Carbon-13 nuclear magnetic resonance spectroscopy of *Cephalotaxus* alkaloids. Organic Magnetic Resonance, 1980, 13(2). 114-115).

[Chemical Formula 1]

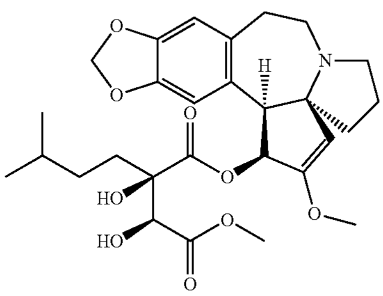

Isolated isoharringtonine is a white powder, ESI-MS 532 [M+H]+, the molecular formula is C28H37NO9. The NMR spectrum is as follows. $^1$H-NMR (500 MHz, CD3OD) δ 6.62 (1H, s, H-17), 6.58 (1H, s, H-14), 5.97 (1H, d, J=9.7 Hz, H-3), 5.82 (1H, d, J=1.1 Hz, H-18a), 5.72 (1H, d, J=1.1 Hz, H-18b), 5.16 (1H, s, H-16), 3.85 (1H, d, J=9.8 Hz, H-4), 3.24 (1H, 1H, m), 3.19 (1H, m, H-8a), 2.91 (1H, m, H-11a), 2.84 (1H, td, J=11.7, 7.2 Hz, H-10a), 2.60 (2H, m, H-8b, H-10b), 2.39 (1H, dd, J=14.4, 6.9 Hz, H-11b), 1.98 (1H, m, H-7a), 1.90 (1H, m, H-6a), 1.78 (1H, m, H-6b), 1.40 (2H, m, H-1"b, H-3"), 1.20 (1H, m, H-2"a), 0.98 (1H, m, H-2"b), 0.82 (1H, d, J=6.7 Hz, H-4"), 0.81 (1H, d, J=6.7 Hz, H-5"); $^{13}$C NMR (125 MHz, CD3OD) 173.5 (C-1'), 172.9 (C-4'), 160.1 (C-2), 148.1 (C-15), 147.1 (C-16), 134.3 (C-13), 129.9 (C-12), 114.2 (C-14), 110.9 (C-17), 102.0 (C-18), 100.6 (C-1), 80.7 (C-2'), 75.9 (C-3), 75.3 (C-3'), 72.2 (C-5), 57.7 (C-19), 56.2 (C-4), 54.5 (C-8), 52.2 (C-5'), 49.8 (C-10), 43.7 (C-6), 34.8 (C-1"), 32.7 (C-2"), 32.0 (C-11), 29.4 (C-3"), 23.2 (C-4"), 22.7 (C-5"), 20.7 (C-7).

Figure 2:
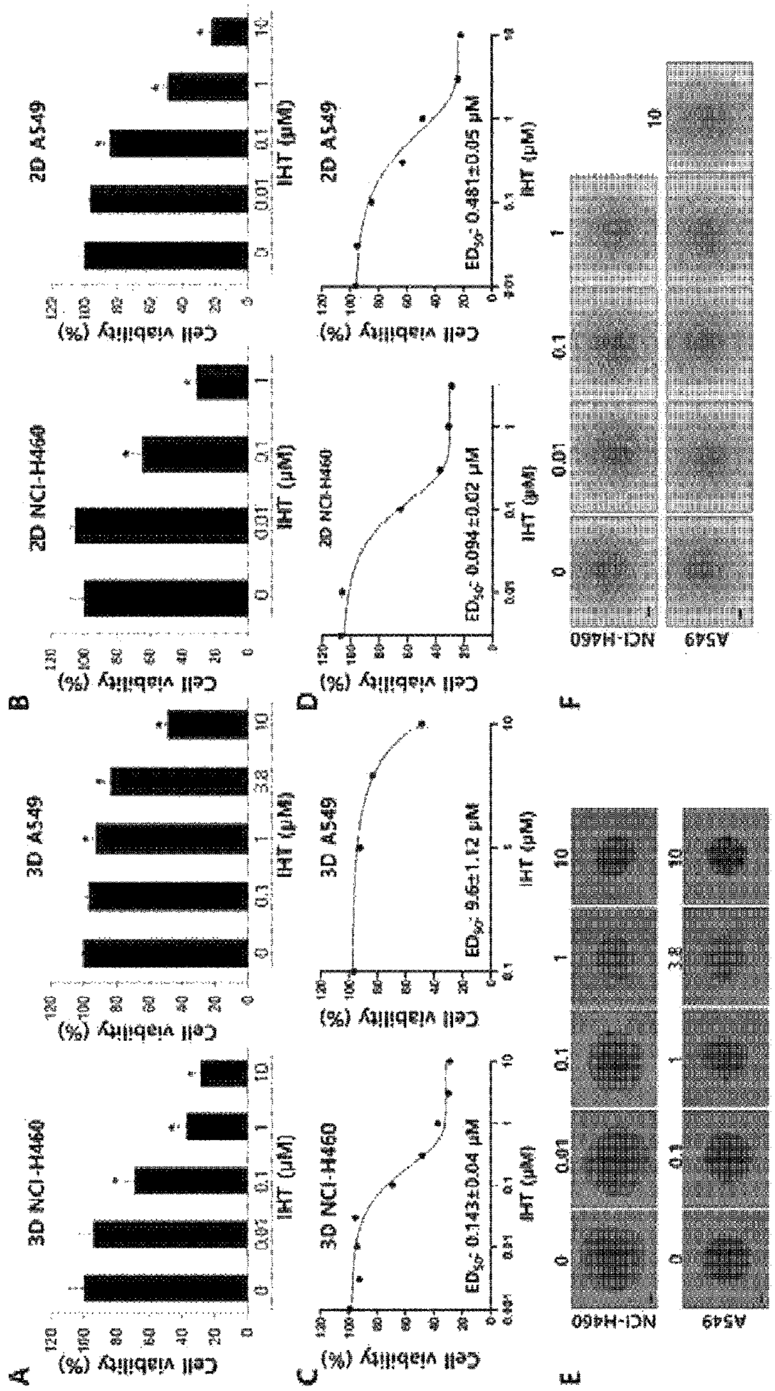
FIG. 2 shows the growth inhibitory effect of isoharringtonine (IHT) on non-small cell lung cancer cell lines.

[Example 1] Effect of Isoharringtonine (IHT) on Growth Inhibitory of Non-Small Cell Lung Cancer Cell Line A549 and NCI-H460 cell lines were placed in 96-well ultra-low attachment (ULA) plates at 7,000 and 1500 cells/well, and centrifuged at 1000 rpm for 10 minutes. Then, they were cultured in Roswell Park Memorial Institute (RPMI) 1640 medium mixed with 0.5% Matrigel, 10% Fetal Bovine Serum (FBS), and 1× penicillin-streptomycin for 2 days. They were treated with IHT, and the degree of cell growth was measured with CellTiter-Glo 3D (Promega, Madison, WI, USA) reagent after 72 hours, and 2D cultured cells were exposed to IHT at the indicated concentration for 48 hours, and then the cell growth was measured with CellTiter-Glo reagent. The average effective dose ED50 of IHT was determined by analyzing the dose-response curve with GraphPad Prism, and the results are shown in FIG. 2. The scale bar was 100 μm, and all data were expressed as mean±standard deviation.

Looking at FIG. 2, it can be confirmed that when IHT was treated onto the three-dimensional tumorspheroid of NCI-H460, the growth of tumorspheroids was inhibited in a dose-dependent manner, and the average effective amount (ED50) was 0.143±0.04 μM (FIGS. 2A, C and E). Growth inhibition of A549 tumorspheroid was also induced, but less effective than that of NCI-H460, and ED50 was predicted to be 9.6±1.12 μM (FIGS. 2B, D and F). In addition, it was confirmed that during 2D culture, IHT more effectively reduced cell proliferation in a dose-dependent manner in both cell lines, and ED50 was calculated to be 0.094±0.02 μM for NCI-H460 and 0.481±0.05 μM for A549.

Thereby, it was confirmed that isoharringtonine exhibited an inhibitory effect on the proliferation of non-small cell lung cancer cell lines.

Figure 3:
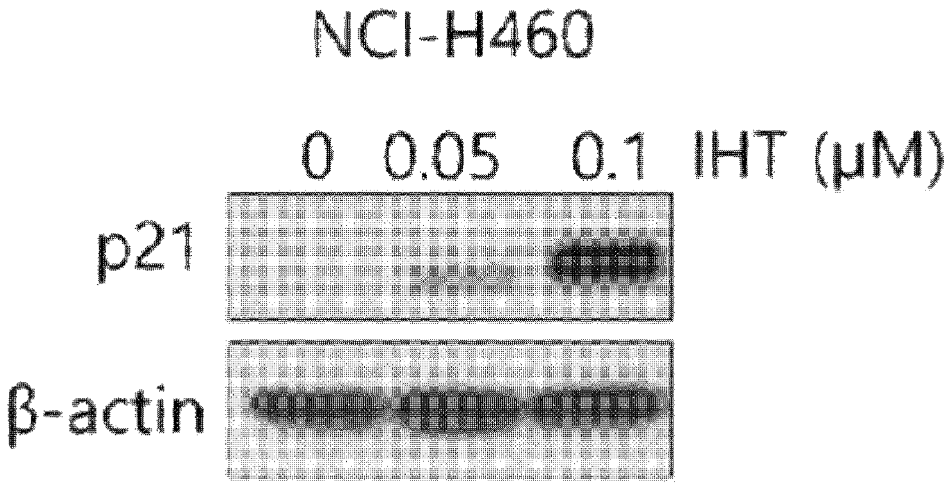
FIG. 3 shows the effect of isoharringtonine (IHT) on the induction of an increase in p21 protein.

[Example 2] Effect of Isoharringtonine (IHT) on the Induction of an Increase in p21 Protein NCI-H460 cell line was cultured in 2D, treated with IHT at the indicated concentration for 48 hours, and then Western blots were performed to measure changes in p21 protein. The results are shown in FIG. 3.

The cells were dissolved in a RIPA (radio immunoprecipitation) buffer containing protease inhibitors, phosphatase inhibitors, PMSF (phenylmethylsulfonyl fluoride), and DTT (dithiothreitol), and protein concentration was quantified with a micro BCA test kit. Equal amounts of protein was added to a polyacrylamide gel containing SDS (Sodium dodecyl sulphate), isolated by electrophoresis, and transferred to a polyvinylidene difluoride (PVDF) membrane. The membrane was blocked with a solution containing 5%-TBST (tris-buffered saline with Tween20) milk, and the primary antibody was exposed at 4 degrees Celsius for 16 hours.

The antibodies used were as follows: β-actin (sc-477778), p53 (sc-126), Bax (sc-526) (Santacruz Biotechnology); cleaved caspase-7 (Asp198) (#9491), cleaved poly (ADP-ribose) polymerase (PARP) (#9541), X chromosome-linked inhibitor of apoptosis (XIAP) (#2045), Survivin (#2808), p21 (#2947), phospho-Akt (#9275), cleaved caspase-9 (#9501), caspase-9 (#9502), caspas-8 (#9746), phospho-Stat3 (#9145) (Cell Signaling Technology).

Subsequently, the membrane was washed with TBSP, and then exposed to the secondary antibody conjugated with HRP (horseradish peroxidase, Santacruz Biotechnology) at room temperature for 1 hour, washed, and film-developed using an ECL (enhanced chemiluminescence, Amersham) kit to observe the bands.

Looking at FIG. 3, it was confirmed that NCI-H460 cell line effectively inhibited the cell growth even at low concentrations, and increased p21, a GT-S cell cycle inhibitor at low concentrations below the ED50. These results suggested inhibiting p21-induced GT-S cell cycle transition as one of the mechanisms of cell growth reduction.

[Example 3] Effect of Isoharringtonine (IHT) on the Growth Inhibition and Cell Death Induction of Tumorspheroids 1. Effects of IHT on the Growth Inhibition and Cell Death Induction of Tumorspheroids After IHT was treated onto the 3D tumorspheroid of NCI-H460, or siNR4A1 and IHT were treated in combination on the 3D tumorspheroid of A549, the growth inhibition and cell death induction of tumorspheroids were observed. Negative control (siNC) or siNR4AT-transfected A549 and non-transfected NCI-H460 tumorspheroids were treated with IHT at each concentration, and after 48 and 72 hours, the cell growth was measured using CellTiter-Glo 3D cell viability assay kit (Promega). A549 cells were transfected with 20M siRNA using Lipofectamine 2000 (Invitrogen), and siNR4A1 of SEQ ID NO: 1 (5'-GAGCUAUUC-CAUGCCUACG-3') and SEQ ID NO: 2 (5'-GGAUACUG-GAUACACCCGU-3') were mixed and used.

After the IHT was treated with NCI-H460 and A549 tumorspheroids for 72 hours, the cell death was observed using LIVE/DEAD Viability/Cytotoxicity Kit (Thermo Scientific). Live cells were stained with green fluorescence-labeled calcein-AM, dead cells were stained with red fluorescence-labeled ethidium homodimer-1 (EthD-1), and images were taken at 100× magnification using the Operetta High Content Screening (HCS) System. The results are shown in FIG. 4. Scale bar was 200 μm, and all data were expressed as mean±standard deviation. * P<0.05, shows a significant difference compared to the control group.

Looking at FIG. 4, when treated with 1,3,5 uM of IHT and then observed for 48 and 72 hours, it was confirmed that the growth inhibition (FIG. 4A) and cell death of NCI-H460 tumorspheroids were effectively induced at all concentrations (FIG. 4B), and the treatment of IHT alone onto A549 tumorspheroids did not have a significant growth-inhibitory effect, but further inhibition of NR4A1 expression using siRNA exhibited a rapid growth-inhibitory effect even at a low concentration (1 uM) (FIG. 4A). In addition, it was confirmed that treatment of IHT alone onto the A549 tumorspheroids did not induce cell death, but further inhibition of NR4A1 expression sharply induced cell death even at a low concentration (1 uM) (FIG. 4C).

2. Confirmation of Apoptosis Induced in Tumorspheroids

An experiment was designed to confirm whether cell death induced in 3D tumorspheroids was apoptosis. Induction of apoptosis was examined after treating NCI-H460 tumorspheroids with IHT or treating A549 tumorspheroids with IHT along with siNC or siNR4A1. NCI-H460 and siRNA-treated A549 tumorspheroids were treated with IHT at the indicated concentrations for 72 hours, and then apoptosis was measured using a Cell Death detection ELISA kit. Further, after IHT treatment for 72 hours, single cells were isolated from tumorspheroids, stained with Annexin V and 7-AAD, and analyzed by a flow cytometry. Apoptotic cell population was represented as the ratio of cells in the early apoptotic processes that are annexin V-positive/7-AAD-negative, and terminal apoptotic process positive for both annexin V/7-AAD (FIG. 5). All data are expressed as mean±standard deviation. *p<0.05 indicates a significant difference compared to a control group, and **p<0.01 indicates a significant difference compared to a control group.

Looking at FIG. 5, it was proven that the cell death observed in FIG. 4 was apoptosis using a cell death detection ELISA kit that measures the amount of DNA fragments produced upon induction of apoptosis (FIG. 5A). In the NCI-H460 tumorspheroid, apoptosis also increased from 1 uM in a dose-dependent manner during IHT treatment in the same manner as the cell death observed in FIG. 4. On the other hand, in A549 tumorspheroids, apoptosis was not induced when treated with IHT alone in the same manner as the cell death observed in FIG. 4, but simultaneous treatment with siNR4A1 sharply increased apoptosis even at a low concentration (1 uM).

Further, using the phenomenon that annexin V was exposed to the outside of the cell membrane in the early stage of apoptosis, cells were stained with annexin V, stained with 7-Amino-Actinomycin D (7-AAD) penetrating into dead cells, and analyzed with a flow cytometry, thus showing apoptosis and cell death. As a result, it was observed that A549 tumorspheroid did not induce apoptosis when treated with IHT alone, but simultaneous treatment with siNR4A1 sharply increased apoptosis even at low concentrations (1 μM).

3. Analysis of the Apoptosis-Inducing Mechanism of Isoharringtonine (IHT)

In the induction of apoptosis by the intrinsic pathway, a decisive process is the release of cytochrome C inside mitochondria to the outside due to changes in mitochondrial membrane potential. After 48 hours of treatment to measure mitochondrial membrane potential changes, tumorspheroids were isolated into single cells and stained with JC-1, and flow cytometry was used to measure the percentage of mitochondria-damaged cells. The percentage of cells in which JC-lexists as a single entity, meaning a decrease in mitochondrial membrane potential, was indicated. In addition, A549 tumorspheroids transfected with negative control (siNC) or siNR4A1 and NCI-H460 tumorspheroids were treated with IHT for 48 hours, and then subjected to Western blot analysis for apoptosis-related protein changes, and the results are shown in FIG. 6. All data are expressed as mean±standard deviation, and *p<0.05 shows a significant difference compared to a control group.

As shown in FIG. 6, changes in mitochondrial membrane potential were induced in NCI-H460 tumorspheroids when treated with 3 uM IHT, and simultaneous treatment of A549 tumorspheroids with IHT and siNR4A1 induced a decrease in mitochondrial membrane potential even at a low concentration (1 uM). (FIG. 6A). This result proves that IHT activates the intrinsic pathway via mitochondria to induce apoptosis.

Upon activation of the intrinsic pathway, pro-caspase-9 is cleaved and caspase-9 is activated, and upon activation of the extrinsic apoptosis pathway, caspase-8 is activated. As shown in FIG. 6B, treatment of IHT (NCI-H460) and IHT+siNR4A1 (A549) induced the cleavage of caspoase-9 and thus, it was proven that the intrinsic apoptotic pathway is activated. In addition, it was confirmed that IHT induces an increase in p53, which induces cell death, in NCI-H460 tumorspheroids, and induces the reduction of Bcl-2 and Mcl-1, which play an important role in inhibiting endogenous apoptosis, along with the reduction of phospho-Akt, which is important for cell survival, and induces the decrease of Survivin and XIAP, which inhibit caspase. A549 tumorspheroids treated with both IHT and siNR4A1NA induced a reduction of Mcl-1 and XIAP together with a reduction of phospho-Akt.

These results confirmed that IHT activates the intrinsic pathway via mitochondria to induce apoptosis.

[Example 4] Combined Therapeutic Effect of Isoharringtonine (IHT) and siNR4A1

In non-small cell lung cancer patients with EGFR (epidermal growth factor receptor) exon21 mutation (L858R), the therapeutic effect of EGFR-TKI (tyrosine kinase inhibitor) is excellent. However, tolerance develops quickly, one mechanism of which is because the second mutation (L858R, T790M) occurs in EGFR. *C. elegans* with EGFR double mutation (L858R, T790M) causes cell proliferation (multivulva formation). It was observed whether cell proliferation could be inhibited upon IHT treatment. This is an in vivo system that can predict the therapeutic effect of lung cancer resistant to EGFR-TKIs, by introducing genetic mutations observed in cells showing drug resistance to the EGFR-TKI (tyrosine kinase inhibitor) used as a therapeutic agent for human lung cancer.

To confirm the in vivo anticancer activity of high concentrations of IHT or low concentrations of IHT and siNR4A1, L1 larvae of jgIs25 (EGFR T790M-L858R) were treated with liquid medium at the indicated concentrations, and the number of Muv-bearing adult larvae was counted and displayed. After IHT treatment to *C. elegans* jgIs25, observations were performed using a differential interference contrast (DIC) microscope. 0.5% DMSO was used as a vehicle control. Arrowhead indicates normal vulva, whereas arrow indicates multivulva (Muv) exhibiting overgrowth. In addition, jgls2 L4 larvae were transferred to DMSO, nhr-6 RNAi, IHT, or nhr-6 RNAi+IHT medium, and the number of Muv-bearing F1 adult larvae was counted and displayed. 0.1% DMSO as a control or 5 μM IHT was. Data are expressed as mean±standard error, P<0.01 and *P<0.001.

Further, A549 cells ($5\times10^6$) were inoculated into the dorsal side of athymic nude mice, and when the tumor size reached 100-150 $mm^3$, siRNA (50 pmoles) and IHT (500 ng) were intratumorally administered once a week and twice a week, respectively, for 4 weeks. The tumor size was monitored twice a week, and tumor volume was calculated by the following Equation 3. Data are expressed as mean±standard error. #P<0.05 shows a significant difference between the siNC+veh group and the siNC+IHT group, and *P<0.05 shows a significant difference between the siNC+veh group and the siNR4A1+IHT group.

$$V(mm^3)=length\times width\times width/2 \quad \text{[Equation 3]}$$

When *C. elegans* jgIs25 strain was treated with IHT, multivulva formation was not inhibited at a low concentration (5 uM), but multivulva formation was significantly inhibited at high concentrations (FIG. 7A). *C. elegans* homologue of the human NR4A1 gene is the nhr-6 gene, and when sinhr-6 was treated at low IHT concentrations, multivulva formation was significantly inhibited. Altogether, it predicts that high-concentration IHT or the combination of low-concentration IHT and siNR4A1 would be effective against EGFR-TKI resistance-induced lung cancer (FIG. 7B). Furthermore, xenograft tumors generated with A549 cell line were treated with low concentrations of IHT (20 μg/kg) and siNR4A1 and tumor suppressive effects were observed (FIG. 7C).

Through these results, it was confirmed that anticancer activity was exhibited not only when treated with high concentrations of IHT but also when treated with low concentrations of IHT and siNR4A1 in combination.

[Example 5] Combination Effect of Isoharringtonine (IHT) and Cisplatin

A549 tumorspheroids were grown for 3 days, then subjected to the combined treatment of cisplatin and IHT at the indicated concentrations. Cell growth was measured after 3 days, and the results are shown in FIG. 8. †P<0.05 shows a significant difference compared to the control group, #P<0.05 shows a significant difference compared to 1 μM IHT, and *P<0.05 shows a significant difference compared to 10 μM IHT.

FIG. 8 shows that a significant but minute inhibition of growth was induced at a high concentration of 30 μM cisplatin, but when used in combination with 1 μM IHT, the cell growth was inhibited by about 48%. When treated with 10 μM IHT, the cell growth was very effectively inhibited, and when used in combination with low concentration of 10 μM cisplatin, it exhibited stronger inhibition of cell growth. That is, it was confirmed that A549 tumorspheroids, which has low sensitivity to cisplatin, were induced to undergo apoptosis when treated in combination with IHT.

This example indicates that IHT sensitized cancer cells to cisplatin and further suggests that combination treatment with low concentration of cisplatin induces a dramatic anticancer effect and thus low toxicity.

The invention claimed is:

1. A pharmaceutical composition comprising a pharmaceutically effective amount of isoharringtonine and a pharmaceutically effective amount of siNR4A1.

2. The pharmaceutical composition according to claim 1, wherein the pharmaceutical composition is formulated for oral administration to a subject.

3. The pharmaceutical composition according to claim 1, wherein the pharmaceutical composition is formulated for parenteral administration to a subject.

4. A method of treating lung cancer in a subject, the method comprising:

A) administering a pharmaceutical composition comprising a pharmaceutically effective amount of isoharringtonine to the subject; and B) administering siNR4A1 to the subject.

5. The method according to claim 4, wherein the pharmaceutical composition is formulated for oral administration.

6. The method according to claim 4, wherein the pharmaceutical composition is formulated for parenteral administration.

7. The method according to claim 4, wherein the lung cancer is a non-small cell lung cancer.

8. The method according to claim 4, wherein the lung cancer is a lung cancer showing resistance to EGFR-TKIs.

9. The method according to claim 4, wherein the method comprises inhibiting tumorspheroid growth through apoptosis in the subject.

10. The method of claim 4, further comprising administering cisplatin to the subject.

11. A method of treating lung cancer in a subject, the method comprising:

A) administering a health functional food comprising a pharmaceutically effective amount of isoharringtonine to the subject; and B) administering siNR4A1 to the subject.

12. The method according to claim 11, wherein the lung cancer is a non-small cell lung cancer.

13. The method according to claim 11, wherein the lung cancer is a lung cancer showing resistance to EGFR-TKIs.

14. The method according to claim 11, wherein the method comprises inhibiting tumorspheroid growth through apoptosis in the subject.

15. The method of claim 11, further comprising administering cisplatin to the subject.

* * * * *